United States Patent [19]

Gallegra

[11] 3,956,349

[45] May 11, 1976

[54] PROCESS FOR PREPARING 3-ENOL ETHERS OF 11β-HYDROXY-Δ⁴-PREGNENE-3-ONES AND DERIVATIVES THEREOF

[75] Inventor: Pasquale G. Gallegra, San Jose, Calif.

[73] Assignee: Syntex (U.S.A.) Inc., Palo Alto, Calif.

[22] Filed: Feb. 18, 1975

[21] Appl. No.: 550,245

[52] U.S. Cl.................. 260/397.45; 260/239.55 D
[51] Int. Cl.²........................................... C07J 71/00
[58] Field of Search............... 260/397.45, 239.55 D

[56] References Cited
OTHER PUBLICATIONS
"J.A.C.S.," Vol. 81 (1959), article by Villotti et al., p. 4569.

*Primary Examiner*—Elbert L. Roberts
*Attorney, Agent, or Firm*—Tom M. Moran

[57] ABSTRACT

3-enol ethers of 11β-hydroxy-Δ⁴-pregnene-3-ones are prepared by reacting triethylorthoacetate with an 11β-hydroxy-Δ⁴-pregnene-3-one in a solvent which is at least 40% by weight or more ethanol and 60% by weight or less of a compatible oxygenated hydrocarbon liquid in the presence of an acid catalyst. This reaction forms a basis of a process for forming 6-halo-derivatives, particularly 6-chloro-$\Delta^{1,4,6}$-pregnatrien-11β,17α,21-triol-3,20-dione.

18 Claims, No Drawings

PROCESS FOR PREPARING 3-ENOL ETHERS OF 11β-HYDROXY-Δ⁴-PREGNENE-3-ONES AND DERIVATIVES THEREOF

BACKGROUND OF THE INVENTION

1. Field Of The Invention

The primary aspect of this invention is a process for forming 3-enol-ethers from 3-oxo-$\Delta^4$-11-hydroxy steroidal compounds by reacting the 3-oxo-$\Delta^4$-11-hydroxy steroid with triethyl orthoacetate in the presence of a substantial amount of ethanol. This aspect contributes to a novel process for preparing 6-halo-$\Delta^{4,6}$- and $\Delta^{1,4,6}$-pregnatrienes, particularly the 6-chloro-$\Delta^{1,4,6}$-pregnatriene-11,17α,21-triol-3,20-diones and the corresponding 21-acetates.

2. Prior Art

In the preparation of active steroidal compounds for use as, for example anti-inflammatory drugs, it is often necessary to start with a readily obtainable compound, then performing a substantial number of steps which steps might include reacting one moiety of the compound to form a protecting group then reacting another moiety of the compound as desired. Through this procedure an extensive series of steps may be required to obtain the desired product and at each step there are certain yield losses which carried over the various steps may amount to a substantial and expensive yield loss over the entire process. Thus, in the field of steroid chemistry, researchers constantly work to develop more effective reaction schemes to increase overall yields by decreasing the number of steps required in a reaction sequence, by increasing yield for any particular step, or both. The overall yield may be improved either by providing a process wherein substantially all the starting material is reacted to form the desired product or side reactions are minimized.

An important step in many reaction sequences to form a 6-halo-$\Delta^{4,6}$- or $\Delta^{1,4,6}$-pregnatriene involves the conversion of a "cortisol-like" compound having a 3-oxo-$\Delta^4$ group to an enolether (i.e. formation of a 3-alkoxy-$\Delta^{3,5}$intermediate) by reacting the 3-keto-$\Delta^4$-steroid with a lower alkyl orthoformate in a suitable solvent such as dioxane in the presence of an acid catalyst such as p-toluenesulfonic acid. However, in starting from a readily available compound such as cortisol (hydrocortisone; 11β, 17α, 21-trihydroxy-3,20-dioxopregn-4-ene) which has a reactive hydroxy at 21 and 11β, it has previously been shown that it is preferable to first react the cortisol (indicated as I, below) with formaldehyde and methylene chloride in hydrochloric acid to form a bis-methylenedioxy-(BMD) compound indicated as II below, i.e.

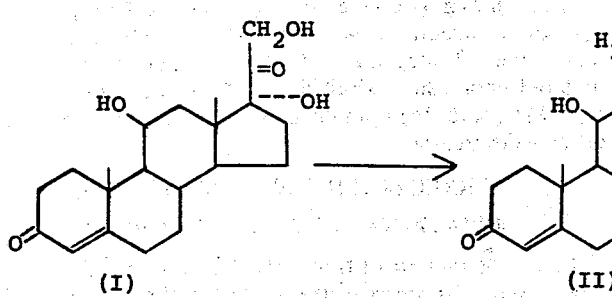

See for example U.S. Pat. Nos. 2,888,456 and 288,457, both to Beryler and Sarett of Merck.

To then prevent the formation of a $\Delta^{11(9)}$ derivative during the subsequent reaction with the lower alkyl orthoformate in acid through dehydration of the OH at 11β and the H at 9, the 11β-OH is first oxidized with e.g. chromic acid in sulfuric acid in dimethylformamide (DMF), i.e.

(II) ⟶ 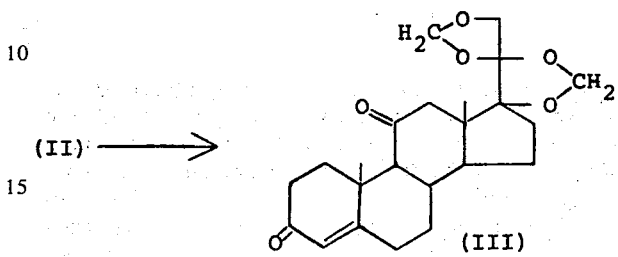

Compound III is then treated with the lower alkyl orthoformate and acid to form the desired enol-ether (IV) which then may be treated further as required, i.e.

(III) ⟶ 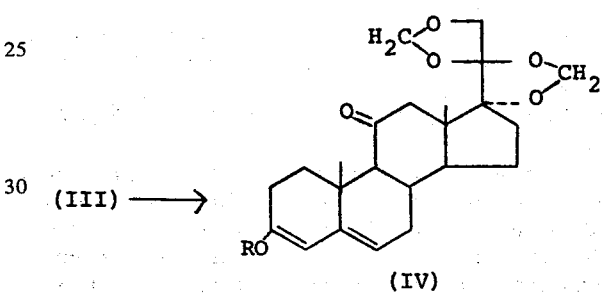

where R = lower alkyl

It has been suggested in U.S. Pat. No. 3,082,224 to Weinstock that the dehydration problem can be solved by reacting a cortisol or cortisol 21-ether with a lower alkyl orthoformate in a solvent consisting solely of the corresponding lower alkanol and an acid catalyst. Employing this method, dehydration may allegedly be reduced to less than 10% and the 3-enol ether may be obtained in yields of 65% to 90%.

Another patent which discusses the formation of the intermediate 3-enol ether of the type mentioned above is U.S. Pat. No. 3,087,927. In that reaction sequence, the starting material was, e.g., 16-hydroxy cortisol or 16-hydroxy-cortisone. The patent discloses that these materials may be reacted in the presence of a mineral acid with an orthoester of the formula

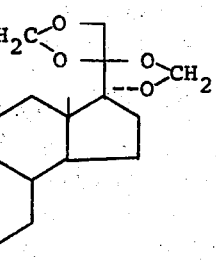

wherein $R^3$ is H or lower alkyl (C 1–3) and $R^4$ is lower alkyl such as methyl and ethyl, to give a reaction product such as

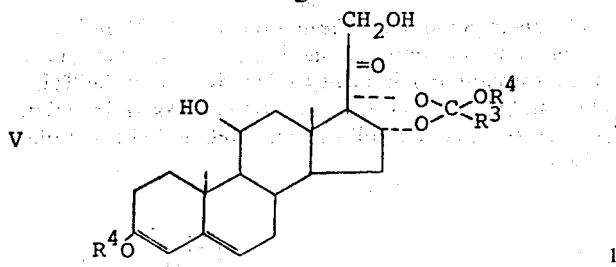

Specifically, the examples show the reaction is carried out in dioxane with a small amount of methanol and sulfuric acid with trimethyl orthoformate. No mention is made in the disclosure of the patent of the dehydration problem discussed in U.S. Pat. No. 3,082,224.

Thus the prior art suggests that 11-hydroxy-Δ⁴-pregnene-3-ones could be reacted to form the corresponding enol ether by using:

1. trialkyl orthoformate using a major amount of a solvent such as dioxane and a minor amount of the corresponding lower alkanol (i.e. trimethyl orthoformate with methanol or triethyl orthoformate with ethanol),
2. using triethyl orthoacetate with a major amount of a solvent such as dioxane with a minor amount of ethanol or,
3. using triethyl orthoformate with ethanol as the sole solvent.

In each of these cases an acid catalyst is used to allow the reaction to go at the desired rate. It has been found that in the first case the major product is the Δ⁹⁽¹¹⁾ dehydration product, in the second case the reactants do not react, and in the third case there is some dehydration which takes place between the 11 and 9 position and the reaction does not go to completion. Thus in each reaction known in the art the yields of the desired enol ether are low and in an extensive sequence of steps, this yield of course, will be carried through and will cut down on the overall production of the desired end product.

It has now been found that by using the process of this invention to form a 3-enol-ether from a 3-oxo-Δ⁴-11β-hydroxy steroid the following advantages are realized:

1. Dehydration at the 9(11) position is substantially completely eliminated;
2. Because of (1) there is no need to first oxidize the 11-hydroxy to an oxo group for purposes of protection;
3. Yield of the enol-ether is increased (due in part to 1 and 2, above, and also due in part to the tendency of the reaction of the process of this invention to go to completion);
4. Inexpensive oxygenated hydrocarbon cosolvents such as glymes may be used with ethanol;
5. In reacting steroids having 17α,21-hydroxy moieties it is not necessary to protect these moieties via BMD or other methods; and
6. The above 5, advantages all contribute to a simpler process than previously known in the art.

Other advantages of the process of this invention will be apparent to those skilled in the art from reading the disclosure below.

SUMMARY OF THE INVENTION

The primary aspect of this invention is a process for preparing 3-enol ethyl ethers which are useful as intermediates in the formation of therapeutically active 6-halo-Δ¹,⁴,⁶-pregnatriene-3-ones. Another aspect of the invention is a process for preparing 6-halo-Δ⁴-pregnene-3-ones also useful as intermediates in the preparation of said 6-halo-Δ¹,⁴,⁶-pregnatriene-3-ones. Still another aspect of this is a particularly effective overall process for the preparation of 6-halo-Δ⁴,⁶-pregnadiene-3-ones and said 6-halo-Δ¹,⁴,⁶-pregnatriene-3-ones.

The primary aspect of this invention is a process which comprises reacting a compound of the formula

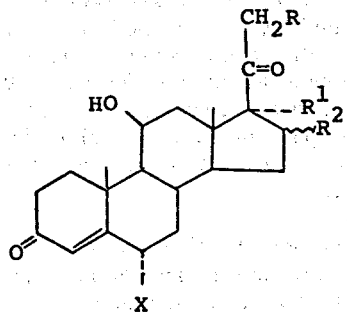

R is H, OH, OR³, or $$\underset{\parallel}{O}\atop OCR^3;$$

R¹ is H, OH, or $$\underset{\parallel}{O}\atop OCR^6;$$

R² is H, α—CH₃, or β—CH₃
R³ is lower alkyl of 1 to 6 carbon atoms or lower alkyl ester of 1 to 6 carbons;
R⁶ is lower alkyl of 1 to 6 carbon atoms;
X is H, F, Cl or Br; and
R¹ and R² together may be $$\begin{matrix}-O\\ -O\end{matrix}\!\!>\!\!C\!\!<\!\!\begin{matrix}R^4\\ R^5\end{matrix}$$

where
R⁴ and R⁵ are independently hydrocarbons of 1 to 4 carbons with triethyl orthoacetate in the presence of a catalytic amount of a strong acid in a solvent which is at least 40% by weight or more ethanol and 60% by weight or less of a compatible, oxygenated hydrocarbon liquid. Preferably the solvent is a 50/50 mixture of ethanol and glyme and the catalyst is a strong organic acid such as p-toluene sulfonic acid or trifluoroacetic acid. The process is particularly useful for cortisol and cortisol-21-alkyl esters such as the 21-acetate.

The resulting 3-enol ether is then halogenated, preferably chlorinated, to form the corresponding 6β-halo-Δ⁴-pregnene-3-one, which in turn is treated to form a 6-halo-3-enol ether, which is then converted to a 6-halo-Δ⁴,⁶ (or Δ¹,⁴,⁶)-pregnadiene (or -triene)-3-one as discussed hereafter.

PREFERRED EMBODIMENTS
FORMATION OF THE 3-ENOLETHER

It is important to utilize triethyl orthoacetate as a reactant in the process of this invention. Triethyl orthoacetate is to be distinguished over the analogous triethyl orthoformate. Triethyl orthoacetate is represented by the following structure:

$CH_3C(OCH_2CH_3)_3$, whereas the triethyl orthoformate is generally characterized as having the following formula:

$HC(OCH_2CH_3)_3$

The chemistry such as the preparation and general reactions of the Aliphatic Orthoesters is discussed in a book entitled "The Chemistry of Aliphatic Orthoesters", American Chemical Society Monograph by H. W. Post, published by Rienhold. Generally the triethyl orthoacetate can be prepared by several methods, the two most popular being indicated in the following equations:

$$CH_3\underset{\underset{NH-HCl}{\|}}{C}-OC_2H_5 + 2C_2H_5OH \rightarrow NH_4Cl + CH_3C(OC_2H_5)_3 \quad (1)$$

$$CH_2=C(OC_2H_5)_2 + C_2H_5OH \rightarrow CH_3C(OC_2H_5)_3 \quad 2.$$

Further preparation can be found on page 40 of the above mentioned monograph. The preparations using the reactants of the first above equations can be found in an article in the Journal of the American Chemical Society, 50, 516 (1928) by P. Sah.

Although, in theory the amount of triethyl orthoacetate needed to form the 3-enol ether by the reaction with the 3-oxo-$\Delta^4$-steroid is 1 mole of the orthoacetate for each mole of the steroid, because of the particular type of reaction it appears that at least about 2 moles of the triethyl orthoacetate per mole of steroid are required for the reaction to proceed and preferably at least about 3 moles of the orthoacetate per mole steroid will be employed. No more than about a 5 to 1 ratio will be utilized, since a higher ratio will result in no particular advantage in rate of reaction, etc.

For the process of this invention to properly function it is important that the solvent system used be one in which a substantial amount of the solvent is ethanol, that is more than at least about 40%w and preferably about 50%w of the solvent system is ethanol. Up to 100% ethanol may be used although it is preferable to use a cosolvent as discussed below. Also the system should be substantially anhydrous, i.e. free of water. Other compatible solvents which can be used in the system are solvents which are freely miscible with ethanol in all porportions. These solvents include oxygenated hydrocarbons for example, aliphatic ethers and cyclic ethers such as glycolethers, dioxane, tetrahydrofuran, and tetrahydropyran. Particularly useful in this regard are the dimethylated polyethylene glycols represented by the formula $CH_3O(CH_2CHO)_xCH_3$ where $n$ is an integer from 1 to 4. These compounds are generally referred to as "glymes", i.e. glyme (n=1), diglyme (n=2), triglyme (n=3) and tetraglyme (n=4). Any of these compounds alone or in combintion may be used as a compatible co-solvent with ethanol in the process of this invention. A particularly useful mixture is about 50%w ethanol with about 50%w glyme.

Further it is necessary to include a catalytic amount of a strong organic acid or sulfuric acid as a catalyst in the process of this invention. Suitable organic acid catalysts include p-toluenesulfonic acid (PTSA); 2,4-dinitrobenzenesulfonic acid, trifluoracetic acid, and the like. Preferably PTSA or trifluoroacetic acid will be employed. A catalytic amount of the catalyst is that amount needed to allow the reaction to proceed at a reasonable rate. Generally this amount will be about 0.1 to about 20% of the total weight of the steroid and preferably will be about 10%w.

Reaction conditions under which the process of this reaction may take place are not critical but are generally known in the art. Thus the temperature may range from 0° to 100°C but preferably, will be between about 20° and 40°C since the higher temperatures tend to decrease overall yields due to losses by degradation. The pressure on the reaction mixture may be atmosphereric, subatmospheric or superatmospheric, but generally will be run at atmospheric conditions. The time needed for the process of this invention to substantially be completed is related to the reaction temperature, the reaction going more slowly at lower temperatures, generally anywhere from 5 minutes to about 3 hours may be needed, however at 20°-40°C it will take no more than about one half hour for the entire reaction to take place.

The reaction vessel which can be used in the process of this invention can be either a batch type vessel or a continuous vessel. Preferably the vessel is an ordinary batch type into which the various materials necessary to carry out the process of the invention are placed and the materials are placed in reactive contact with each other so that the reaction can take place.

The steroids to which the process of this invention is applicable include the 11-hydroxy-$\Delta^4$-pregnene-3-ones which can undergo dehydration between the 11 and 9 carbons of the steroids structure, thus the steroids which are useful in the process of of this invention are of the following structure:

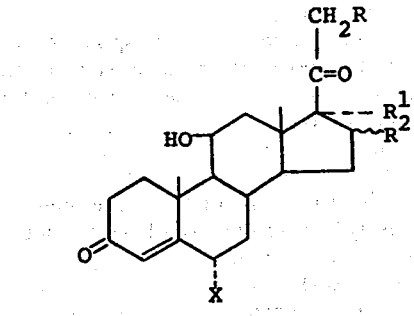

wherein
R is —OH, H, lower alkyl ether of 1–6 carbons, or lower alkyl ester of 1–6 carbons
$R^1$ is —H, OH, or

$R^2$ is —H, $\beta$—$CH_3$ or $\alpha$—$CH_3$;
$R^6$ is lower alkyl of 1 to 6 carbons and may be straight chain or branched;
$R^1$ and $R^2$ taken together may be

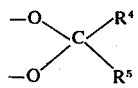

where
R[4] and R[5] are independently H or a hydrocarbon of 1 to 4 carbons. X is F, Cl, Br or H The process of this invention is particularly useful in forming 3-enol ethers intermediate to the formation of active steroid compounds which exhibit anti-inflammatory, anti-androgenic, estrogenic, or other activity, such as those set out in U.S. Pat. No. 3,232,965.

Thus compounds for which the process of this invention are particularly useful for forming the corresponding 3-enol ethylether include the following:

$11\beta,17\alpha$-dihydroxy progesterone;
$11\beta,17\alpha$-dihydroxy-$16\beta$-methyl progesterone;
$11\beta,17\alpha$-dihydroxy-$16\alpha$-methyl-progesterone;
$11\beta,17\alpha$-dihydroxy-$16\alpha$-methyl-progesterone-17-acetate;
corticosterone ($11\beta$,21-dihydroxy-3,20-dioxopregn-4-ene);
corticosterone-21-acetate
cortisol ($11\beta,17\alpha$,21-trihydroxy-3,20-dioxopregn-4-ene);
$16\alpha$-hydroxy-cortisol-16,17-acetonide
$16\alpha$-hydroxy-cortisol-16,17-acetonide-21-acetate
cortisol-$17\alpha$,21-diacetate
$16\beta$-methyl-cortisol;
$16\alpha$-methyl-cortisol;
$16\alpha$-methyl-cortisol-21-acetate;
cortisol-21-methyl ether;
$16\alpha$-methyl-cortisol-21-hexyl ether;
$16\alpha$-methyl-cortisol-21 acetate;
$16\alpha$-methyl-cortisol-21-pivalate;
cortisol-21-acetate
cortisol-21-propionate;
cortisol-21-butyrate, and the corresponding 6-halo derivatives of the above compounds, such as the 6-bromo, 6-fluoro, and 6-chloro derivatives preferably the chloro and fluoro such as
$6\alpha$-chloro-cortisol
$6\alpha$-fluoro-cortisol
$6\alpha$-fluoro-$16\alpha$-hydroxy-cortisol-16,17-acetonide
$6\alpha$-chloro-$16\alpha$-hydroxy-cortisol-16,17-acetonide
$6\alpha$-fluoro-$16\alpha$-methyl-cortisol
$6\alpha$-chloro-$16\alpha$-methyl-cortisol
$6\alpha$-fluoro-$16\alpha$-methyl-cortisol-21-acetate
$6\alpha$-chloro-$16\alpha$-methyl-cortisol-21-acetate It should be noted that the process of forming a 3-enol ether by this invention may be used for example with a 3-oxopregn-4-ene being unsubstituted at the $6\alpha$ position or being halo-substituted at the $6\beta$ position. If the process is used in the latter situation, the $6\beta$-halo steroid is placed in the solvent at about ambient temperatures in the presence of the acid catalyst but in the absence of triethyl orthoacetate for a time sufficient to form the $6\alpha$-halo steroid (generally about 10 minutes to an hour, preferably about 20–40 minutes, at room temperature). Then the triethyl orthoacetate is placed in reactive contact with the $6\alpha$-halo steroid in the solvent to form the 3-enol ether.

When the starting steroid structure exhibits a hydroxy group at both the 21 and 17 positions a resulting 3-enol-ether structure represented by

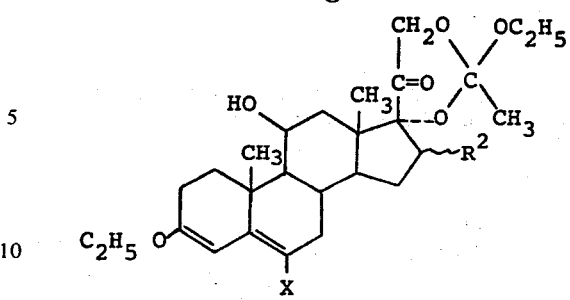

wherein
X and R[2] are defined previously. The presence of such a structure is not detrimental since the 17,21 orthoester is partially hydrolyzed during subsequent steps such as chlorination or bromination, and may be fully converted to the 17,21 dihydroxy by transesterification or under basic conditions. However, such a reaction dose utilize additional triethyl arthoacetate and for economic reasons it is preferable that an alkyl ester e.g. acetate, be at the 21 position.

Reactions of 3-Enol Ethers

Another aspect of the invention is a process for forming 6-halo-$\Delta^4$-pregnene-3-one intermediates by first forming the enol ether as discussed above then halogenating at the 6 position.

Halogenation, that is bromination and, preferably, chlorination, may be carried out by any means known in the art to halogenate at the 6 position. Halogenating agents include N-chlorosuccinimide, N-bromosuccinimide, N,N'-dichlorohydantoin, and the like.

In performing the halogenation step, the 3-enol ether is first isolated from the reactants and solvents of the first step, then the halogenating agent is placed in reactive contact with the 3-enol ether in a suitable inert solvent under conditions sufficient to cause formation of the 6-halo-$\Delta^4$-compound. A suitable, inert solvent is one which does not react with the 3-enol ether or the halogenating agent in a manner detrimental to the reaction. Useful solvents include oxygenated hydrocarbons such as tetrahydrofuran, dioxane, and diethylether, acetone, acetic acid, or mixtures thereof. Preferably the reaction is carried out under neutral conditions i.e. about pH 7 and at temperatures ranging from about $-5°C$ to about $25°C$, preferably at about $0°C$.

More specifically the halogenation may be carried out by reacting the enol ether with dimethyl-N, N'-dichlorohydantoin in a buffered acetone solution at temperatures of from $-5°C$ to about $5°C$ for 60 minutes.

Still another aspect of this invention is a total synthesis for preparation of 6-halo-$\Delta^{4,6}$-pregnadiene-$11\beta,17\alpha$,21-triol-3, 20-diones and 6-halo-$\Delta^{1,4,6}$-pregnatrien-$11\beta,17\alpha$,21-triol-3,20-dione, especially the 6-chloro compounds disclosed in U.S. Pat. No. 3,232,965 to Ringold et al. Both the dienes and trienes have anti-inflammatory action with a minimum of salt retention. The process is also useful for preparing compounds of the $16\alpha,17\alpha$-acetonide series and others using starting compounds listed hereinbefore.

Broadly the total synthesis of this invention may be visualized by referring to the reaction scheme and the following summary.

1. The first step involves esterifying the starting steroid VIII (where R[1] and R[2] are defined above at the 21-hydroxy to form the corresponding 21-alkyl ester (IX).

2. The 21-alkyl ester (IX) is then reacted according to the primary aspect of the process of this invention with triethyl orthoacetate in ethanol and preferably glyme with an acid catalyst to form a 3-enol ether as represented as structure X.

3. The 3-enol ether X is in turn halogenated, i.e. chlorinated or brominated, to form, e.g. a 6β-chloro-Δ⁴-pregnene-3-one, structure XI.

4. Structure XI is then reacted with triethyl orthoacetate in the presence of an acid catalyst in ethanol and preferably glyme to form XII, an enol ether.

5a. the 3-enol ether, XII, may then be treated to form the Δ¹·⁴·⁶-pregnatriene (XIV) directly or 5b. The 3-enol ether, XII, may be first reacted to form the Δ⁴·⁶-pregnadiene XIII.

5c. The Δ⁴·⁶-pregnadiene, XIII, in turn is dehydrogenated by any means known in the art at the 1 position to form the corresponding Δ¹·⁴·⁶-pregnatriene, XIV.

6a. The Δ¹·⁴·⁶-pregnatriene may then be treated to remove the 21-alkyl ester and form the corresponding 21-hydroxy compound, XV, where Z is a double bond, or 6b. XIII may be treated to form the compound XV where Z is a single bond, which in turn may be converted to the Δ¹·⁴·⁶-pregnatriene.

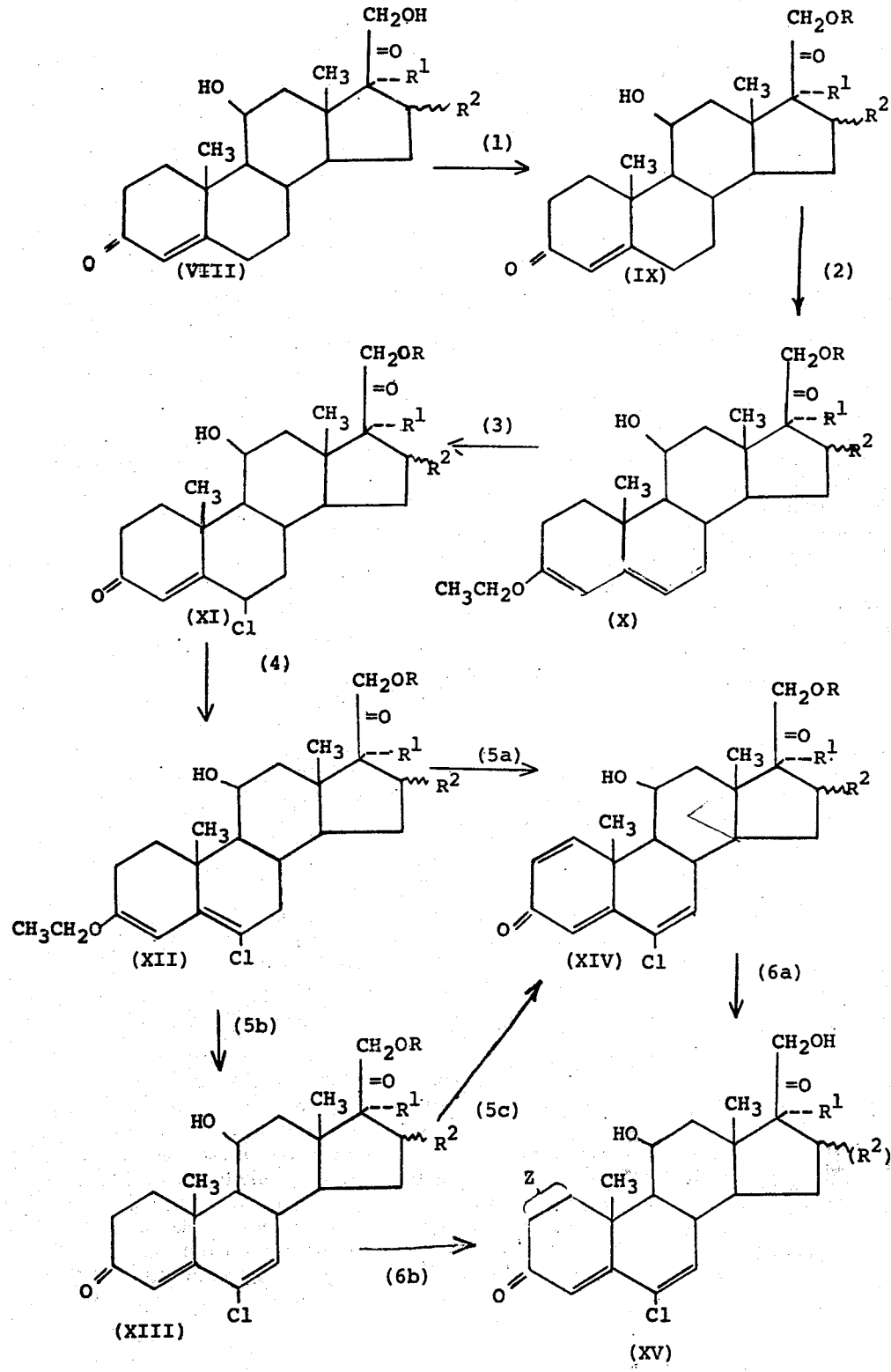

A discussion of each of the steps of the total synthesis follows:

1. In the first step a compound represented by structure XIII, preferably cortisol, is esterified to form a 21 lower alkyl ester having about 2–4 carbons in the ester moiety. This may be done by any suitable method known in the art to esterify at the 21-position. Generally this is done by the reaction of a lower alkyl anhydride in a suitable solvent, for example, the reaction of cortisol with acetic anhydride in pyridine at temperatures of less than 30°C. The reaction is clean and complete and forms a compound represented by sturcture IX which is preferably cortisol-21-acetate. Propionic or butyric anhydride may be used in place of acetic anhydride.

2. In the second step the resulting 21-ester from step 1 is first isolated then reacted with triethyl orthoacetate according to the primary aspect of the process of this invention as discussed above to form the corresponding 3-enol ethyl ether represented by structure X. Preferably sturcture X will be the 3-enol ether of cortisol-21-acetate.

Although it is preferable to first react a compound having a structure such as shown in VIII, e.g. cortisol with acetic anhydride to form the corresponding 21-acetate, the compound represented by structure VIII may be reacted with triethyl orthoacetate at the outset without having to go through the intermediate formation of the 21-acetate. By reacting a compound represented by VIII with triethyl orthoacetate, a small amount, i.e. 10 to 15% of an intermediate 17,21 orthoester is formed, along with the enol ether shown in structure X where R is hydrogen. The presence of the 17,21-orthoester is not detrimental to the overall reaction since it is hydrolyzed at the subsequent step of chlorination under the acidic conditions. However, because the formation of the 17,21-orthoester does react with additional triethyl orthoacetate and because the reaction of a compound such as cortisol with acetic anhydride in pyridine is so clean and the formation of the corresponding 3-enol ethyl ether is complete and fast in step 2 it is preferably first to form the 21 ester before reacting with the triethyl orthoacetate. This preferred route is thus shown in the reaction scheme.

3. After isolating the 3-enol ether (X), it is halogenated to form a 6-halo compound as shown as structure XI. The halogenation step is either a chlorination or bromination step as discussed above.

4. The compound represented by structure XI is a 6β-halo substituted compound. Before this can be reacted with triethyl orthoacetate to efficiently form a 3-enol ether as shown in sturcture XII the halogen must be converted to a 6α-halogen. This is done by placing the 6β-substituted compound (XI) in an inert solvent at about ambient temperatures (20°–25°C), adding a small portion of an acidic catalyst, and maintaining the temperature an hour or less, preferably 30 minutes or less. Preferably this is carried out in a solvent such as glyme in the presence of 1%w or less of a strong organic acid catalyst such as trifluoroacetic acid or p-toluene sulfonic acid. The conversion to the 6α-halo compound is complete within less than an hour, generally less than a half hour. Thereafter ethanol and triethyl orthoacetate are added to the reaction mixture and allowed to react according to the primary aspect of this invention in order to form the 3-enol ether as shown in XII.

After isolation, the intermediate XII may then be converted into the desired end product by various means.

5a. The compound represented by structure XII may be reacted to form the $\Delta^{1,4,6}$-pregnatriene shown in structure XIV directly. In a one step procedure the compound represented by XII may be reacted for example with 2,3-dichloro-4,5-dicyanobenzoquinone (DDQ) and a substantially anhydrous suitable oxygenated hydrocarbon solvent such as dioxane, at room temperature to form the $\Delta^{1,4,6}$-pregnatriene-21-ester represented by XVI which in turn may be hydrolyzed under basic conditions or transesterified to form the 21-hydroxy steroid represented by XV where Z is a double bond.

5b. Because of higher yields, preferably a two step procedure is utilized wherein a structure represented by XIII is first formed which in turn is dehydrogenated at the 1 position to form sturcture XIV. Either of structures XIII or XIV may then by hydrolyzed to form the structure represented as XV wherein Z may be either a single or double bond, respectively. The compound represented by XIII is first formed by reacting XII with a suitable oxidizing agent (a tetrasubstituted 1,4-benzoquinone) at low temperatures (i.e. about 0°–10°C) in a wet oxygenated solvent such as dioxane or acetone with 25% volume or less water. A particularly suitable oxidizing agent is 2,3-dichloro-5,6-dicyanobenzoquinone (DDQ). Generally this reaction will be complete within 2 hours or less.

5c. The 4,6 pregnadien represented by structure XIII is isolated then dehydrogenated at the 1 position to form the compound represented by XIV. The dehydrogenation may be done by chemical or microbiological means which are known in the art. The 4,6-pregnadiene represented by XIII is first isolated before being dehydrogenated according to the next step. In the selective chemical dehydrogenation at the 1 position, compound VIII is reacted with a suitable oxydizing agent under substantially anhydrous conditions in a suitable solvent such as a oxygenated hydrocarbon, for example in alcohol, dioxane, or acetone, at temperatures above room temperature up through refluxing temperatures. A suitable oxidizing agent is DDQ while suitable solvents include xylene, toluene, amyl alcohol, dioxane, or acetone. Preferably the material is refluxed in the solvent for a period of time sufficient to cause the dehydrogenation to take place. This will generally be from 1 hour to about 20 hours, with chloranil in amyl alcohol or about 12 to 16 hours in xylene. With DDQ in anhydrous acetone only about 4 hours will be required at refluxing temperatures.

Preferably, however, the chemical means of dehydrogenating the $\Delta^1$ position will be done by the process of brominating at the 2 position and dehydrobrominating between 1 and 2 to form the double bond. Bromination is done by reacting a suitable brominating agent with the $\Delta^{4,6}$ pregnadiene in a suitable solvent for an amount of time sufficient to complete the reaction. Suitable brominating agents include bromine in combination with hydrogen bromide and can be used in acetic acid at room temperature for a reaction of about 10 minutes which gives a reaction product of about 85% or better.

A particularly valuable brominating agent in the 2-bromination is pyridinium hydrobromide perbromide or trimethyl-phenylammonium tribromide in tetrahydrofuran when run at temperatures of 30°C or less, preferably about 20° to 25°C.

The resulting 2-brominated product is then dehydrobrominated by reacting the 2-bromo product with a dehydrobromanating agent. Typical dehydrobrominating reactions may be found at pp 213–218 of *Steroid Reactions, An Outline For Organic Chemists* by Carl Djerassi, Holden-Day, 1963. As many of those reactions as are pertinent are incorporated herein by reference. A particularly preferred method involves refluxing the 2-bromo-$\Delta^{4,6}$-pregnadiene with lithium carbonate and lithium bromide in DMF for 5 hours or less, preferably less than 3 hours at temperatures of about 100°C to 110°C.

5d. Alternatively the compound represented by structure XIII may be dehydrogenated using microbiological means, that is the compound is treated by a fermentation process which may employ either (i) growing micro organisms such as arthobacter simplex or (ii) cell-free enzyme preparation and lower alkanol or alkane dryed cells in the presence of a hydrogen acceptor. However, because microorganisms and enzyme preparations also have some esterase activity, it is preferable to first form the 21-hydroxy compound by hydrolysis or transesterification, then treat that compound to form the $\Delta^{1,4,6}$ compound.

Representative of the process utilizing a growing microorganism is the process described in U.S. Pat. No. 2,837,464 to Nobile which comprises subjecting a $\Delta^4$-3-keto pregnene to the action of a culture of a member of a group consisting of corynebacterium simplex (also referred to as arthobacter simplex) and corynbacterium hoatii. As much of that patent as is pertinent is incorporated herein by reference. Generally the introduction of a $\Delta^1$ double bond proceeds satisfactorily at pH of 7.6 to about 8 at a temperature of 32° to about 37°C.

Representative of the cell-free enzyme preparation in the presence of hydrogen acceptors is the process which is described in U.S. Pat. No. 3,047,460 to Sih and Bennett. In the process of that patent, a steroid which is saturated in the 1,2 position is subjected to the action of a mixture of a ring A dehydrogenate extract of a microorganism such as corynbacterium, the extract being substantially free of living cells.

Other microorganisms which can be extracted include nocardia, corynbacterium, mycobacterium, cylindrocarpon and bacterium. The hydrogen carriers which may be used along with the cell-free extract in accordance with that invention include oxidation-reduction reagents, for example dyes, such as potassium ferrocyanide; thiazines and imine derivatives as exemplified by methylene blue, phenazine methosulfate and the like; benzoquinones and imine derivatives for example orthoquinone, toluylene blue chloride; naphthoquinones, such as creasal blue and the like; and indophenols, particularly 2,6-dichloroindophenol.

In the cell-free extract process, the extract may be mixed directly with the steroid starting material and the hydrogen carrier then added to the mixture or it may be initially mixed with the hydrogen carrier and then placed in contact with the steroid. A concentration of the hydrogen carrier is not critical and anywhere from a catalytic amount to a stoichiometric amount equal the concentration of steroid may be used. The pH and temperature prevailing during dehydrogenation are not critical. Temperatures may be in the range of 20° to about 45°C, the optimum being around 25° to about 35°C. The pH may be acid, alkaline or neutral and preferably is within the range of 6.0 to 8.0. If desired to maintain the pH of a certain value, a buffering material such as inorganic phosphate, for example sodium phosphate, may be incorporated with the reaction mixture. The reaction mixture is permitted to stand for a suitable period until ring A dehydrogenation has been completed, this normally being within a period of 1 to 20 hours.

A particularly effective dehydrogenation process is discussed in patent application U.S. Ser. No. 550,244 filed even date herewith wherein a $\Delta^{4,6}$-compound such as XV where Z is a single bond is selectively dehydrogenated using arthobacter simplex (also referred to as corynebacterium simplex) in the presence of a hydrogen acceptor such as quinones or quinone derivatives. As much of the disclosure of U.S. Ser. No. 550,244 as is pertinent is disclosed herein by reference. This process is particularly valuable for the preparation of 6-chloro-$\Delta^{1,4,6}$-pregnatrien-11$\beta$,17$\alpha$,21-triol-3,20-dione from the corresponding $\Delta^{4,6}$-pregnadiene. One preferred strain of arthobacter simplex, NRRL No. V-8055 is available to the public and can be obtained from the northern regional research laboratory, 1815 North University Street, Peoria, Ill.

Hydrogen acceptors which are useful in the process of that invention are selected from quinone comounds and derivatives and include benzoquinone such as tetramethyl-p-benzoquinone and 2-isopropyl-5-methyl-p-benzoquinone; naphthoquinones such as menadione and 2-hydroxy-1,4-naphthoquinone; indophenols such as 2,6-dichloroindophenol; and menadione sodium bisulfite. It is advantageous to maintain the pH within a range of about 7.5 to about 8.5 during the $\Delta^1$-dehydrogenation while the temperature whould be about 23° to about 33°C preferably about 28°C. Once a suitable growh medium is obtained a quantity of substrate added to the medium can be as high as 0.7 grams per liter of medium, however, the preferred concentration of substrate is 0.5 grams per liter of medium. The quantity of hydrogen acceptor may vary over a large range, i.e. the molar ratio of substrate to hydrogen acceptor can vary from 30:1 to 10:1. When menadione sodium bisulfite is used as the hydrogen acceptor, the preferred ratio of substrate to acceptor is 15:1.

The steroid can be added to the medium as a suspension in a suitable solvent such as water, as a solution in a solvent such as ethanol, acetone or dimethylformade, or in finely divided form such as solid micronized particles. The hydrogen acceptor is added to the medium as a solution in the solvent such as ethanol or dimethylformamide or in the case of menadione sodium bisulfite as an aqueous solution.

After the addition of substrate and hydrogen acceptor, agitation and aeration of the medium is continued for a period of 3 to 7 hours or until dehydrogenation is complete. During the course of the fermentation reaction, the progress of the dehydrogenation can be monitored by silica gel, thin layer chromatography of solvent extracted samples.

When dehydrogenation is complete, the product, 6-chloro-$\Delta^{1,4,6}$-pregnatriene-11$\beta$,17$\alpha$,21-triol-3,20-dione, is recovered from the fermentation medium by extraction with a suitable solvent such as chloroform, methylene chloride, methyl isobutyl ketone and the like. The solvent solution is evaporated to yield a semi-crystalline product which is purified by silica gel chromatography. The product may be further purified by recrystalization from the suitable solvent such as isopropyl acetate, ethyl acetate, a mixture of acetone and water, and the like.

The following examples are given to illustrate the process of this invention as well as to distinguish the process of this invention over the known processes which exist in the art today. The examples are to be read as being illustrative of representative compounds and conditions only and are not to be read in a limiting sense.

EXAMPLE I 20 grams of cortisol-21-acetate were charged to 100 ml. of absolute ethanol and 100 ml. ethylene glycol dimethyl ether (glyme). The solution was heated to 40°C and 2 grams of p-toluenesulfonic acid (PTSA) followed by 24 grams of triethyl orthoacetate were added. The reaction was stirred at 40°C until solution is effected. The reaction mixture is stirred at 40°C for an additional 20 minutes, cooled to room temperature, and 2 ml. of pyridine are added. The reaction mixture is drowned slowly into a mixture of 520 ml. water and 52 ml. hexane. After 30 minutes at 0°–5°C the product was filtered and washed with water then with 50 ml. of hexane, and the product was dried in vacuum at 40°C. The yield was 90 to 104%. This is an example of the process of this invention which shows that the yields are substantially quantitative for this particular process.

EXAMPLE II

This example is run to show the difference in yield and product between the process of this invention and a process which is known in the art. In this particular example 10 grams of cortisol-21-acetate are charged to 100 ml. of absolute ethanol, 10 ml. of triethyl orthoformate and 0.300 grams of 2,4-dinitrobenzenesulfonic. The mixture is stirred at room temperature until solution is effected. The reaction is stirred for an additional 15 minutes and 1 ml. of pyridine is added. The solution is concentrated to half volume and 10 ml. of water is added. Concentration is continued until crystalization occurs. About 100 ml. of water is added and the product is filtered, washed well with water and dried to give the corresponding 3-enolether. In this particular instance there appeared to be some dehydration product which was completely absent in example 1 and there remained about 10% unreacted material by this process as well as a small amount of other undesired products as compared to Example I wherein there was substantially less unreacted material left according to thin layer chromatography (TLC) determination.

EXAMPLE III

This example shows the necessity of having the triethyl orthoacetate present for the process of this invention to work. In this example the exact technique and amounts of Example I were used except that triethyl orthoformate was substituted for triethyl orthoacetate. Analysis of the end products by thin layer chromatography (TLC) indicated that there was still a small amount of starting material but that there was a substantial amount of intermediates and about 10 to 15% of the $\Delta^{11,(9)}$ dehydration product.

EXAMPLE IV

In this example 20 grams of cortisol were charged to 100 ml. of absolute ethanol and 100 ml. of ethyleneglycol dimethyl ether as in Example I. The remaining procedure set forth in Example I was followed in this example except that 0.3 gram of 2,4-dinitrobenzenesulfonic acid and 10 grams of triethyl orthoacetate were used. Results showed a substantially complete reaction with about 15% of a 17,21-orthoester of the 3-enolether being formed. The presence of this product is not detrimental in the process of this invention since the product can be further reacted and at the end of the series of reactions the 17,21-orthoester can easily be hydrolized to form the corresponding $11\beta,17\alpha,21$-trihydroxy steroid as desired.

EXAMPLE V

The same procedure as Example III was followed except that no ethyleneglycol dimethyl ether was employed. At the end of the reaction sequence there still remained a substantial amount, that is about 10% of the original starting material which was unreacted. Thus again this points out the necessity of having the triethyl orthoacetate present in order for the process of this invention to go to completion.

EXAMPLE VI

This example shows that the process of U.S. Pat. No. 3,087,927 patent does give the desired product.

In order to further establish the importance of the presence of the triethyl orthoacetate and also the importance of a majority of the solvent being ethanol in this example, 30 grams of cortisol-21-acetate are suspended in a solution made up of 300 ml. of dioxane, 30.0 ml. of trimethylorthoformate and 1.20 ml. of absolute methanol. To the rapidly stirred suspension there is added drop wise 0.60 ml. of concentrated sulfuric acid. The suspension thins continuously during the first few minutes and complete solution is effected within six minutes. 1.80 ml. pyridine is added, immediately whereupon a faint pink coloration is discharged and the resulting solution is light yellow in color. The entire process up to this point is carried out at room temperature. The quenched reaction solution is placed in a separatory tunnel, the stem of which is immersed below the surface of 300 ml of water-ice mixture contained in a large beaker. The reaction mixture is added slowly over a period of 2 to 3 hours to the vigorously agitated ice-water mixture. The solid which forms is allowed to stand in the solution at 5°C overnight and is then removed by filtration. The product is washed well with water and air dried, to give 28.7 grams of product. TLC analysis of the product indicated that the entire product is the $\Delta^{9(11)}$ 21-acetate.

EXAMPLE VII

In this example the same procedure of Example VI was followed except that absolute ethanol was used in place of the methanol and triethyl orthoacetate was used in place of the trimethyl orthoformate. By following the procedure of Example VI it was found that there was substantially no reaction. This shows the importance of using a majority of ethanol and that the disclosure of the U.S. Pat. No. 3,086,927 is inoperative.

It can be thus seen from the examples given above and set forth in Table I that the process of this invention wherein the steroid is reacted with the triethyl orthoacetate in a solvent which is comprised of a majority of ethanol and a minor amount of an oxygenated hydrocarbon solvent such as glyme gives results which are superior and unpredictable from the prior art.

Procedure:

A 1-liter flask is charged with 400 ml pyridine and 100 g (0.276 mole) hydrocortisone (cortisol) are added until the cortisol goes partly into solution. While holding the temperature below 30°C, over a period of 10 min, 163.3 g (1.59 mole) acetic anhydride are added. The mixture is aged 1 hr. at room temperature until the reaction is complete. 300 ml water is slowly added to the reaction mixture, keeping the temperature below 40°C. The reaction mixture is aged 20 min and transfered to a 3-liter flask. Over a period of 20 min, 1500 ml saturated aqueous sodium chloride solution is added. The mixture is cooled to 10°C, aged 1 hr and filtered. The product is washed with water and dried at 50°–60°C in vacuum oven. Yield: 110.4 g (110.4w/w; 99.2% Th).

TABLE I

|     |                        | **TEOA | TEOF | EtOH           | GLYME        | H⁺CAT | Results |
|-----|------------------------|--------|------|----------------|--------------|-------|---------|
| I   | (Invention)            | X      | —    | X              | X            | X     | Rxn Complete |
| II  | (Prior Art)            | —      | X    | X              |              | X     | Rxn Incomplete |
| III | (Prior Art)            | —      | X    | X              | X            | X     | Rxn Incomplete; $\Delta^{11(9)}$ dehydration product |
| ✦IV | (Invention)            | X      |      | X              | X            | X     | Rxn Complete; some 17,21-orthoester (not harmful) |
| V   | (Prior Art)            | —      | X    | X              |              | X     | Rxn Incomplete |
| VI  | *(Prior Art-3,087,927) | —      | TMOF | Minor MeOH     | Dioxane      | X     | $\Delta^{11(9)}$ dehydration product only |
| VII | (Prior Art-3,087,927)  | X      |      | Minor          | Dioxane      | X     | No Rxn |

*TMOF = trimethyl orthoformate; less than a percent methanol (MeOH); dioxane used as major solvent.
**TEOA - triethyl orthoacetate
TEOF - triethyl orthoforamate
EtOH - ethanol
H⁺CAT - acid catalyst - varies see each example
Rxn - reaction
"X" - material present
"—" - material absent
✦Cortisol used as starting material

EXAMPLE VIII

The following series of reactions represent a particularly effective method of preparing 6-chloro-$\Delta^{1,4,6}$-pregnatriene-11$\beta$,17$\alpha$,21-triol-3,20-dione from cortisol.

The reaction conditions are representative of those suitable for use in both the narrow and broad aspects of the process of this invention and have been found to be preferable. However, the representative reaction conditions recited in this Example, though preferable, are not to be interpreted in a limiting sense.

Formation Of Cortisol-21-Acetate

Reaction:

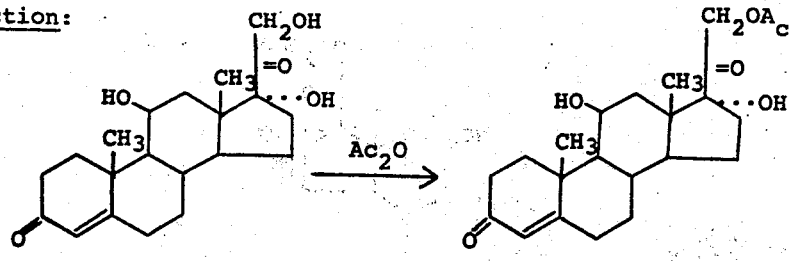

Reaction with triethyl orthoacetate to form the 3-enol ether and subsequent 6β-chlorination

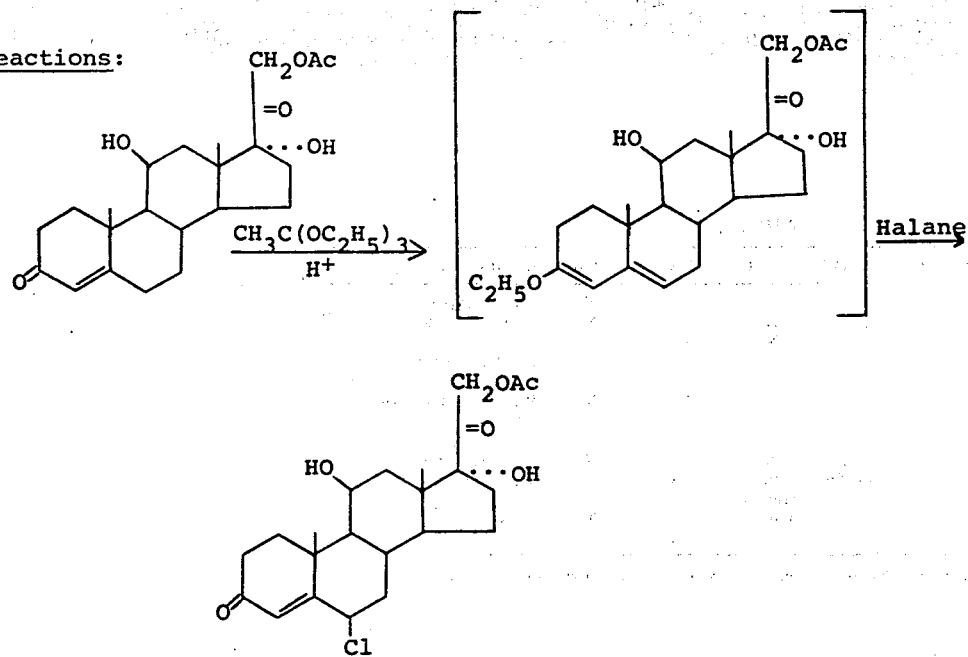

Procedure:

A 2-liter flask is charged with 550 ml ethanol, 330 ml 1,2-dimethoxyethane (glyme) and 110.4 g (0.272 mole) cortisol-21-acetate. The mixture is heated to 40°–42°C and a solution of 9 g p-toluene-sulfonic acid in 200 ml 1,2-dimethoxyethane, followed by 116 g triethylorthoacetate is added. The temperature is kept at 38°–42°C. After 20 min 2.5 g p-toluenesulfonic acid is added. Mixture is aged at 38°–42°C for 30 min, then cooled to 8°–10°C and 12 ml pyridine is added followed by a solution of 2.7 g sodium acetate in 50 ml water. The pale yellow solution is chaged to a mixture of 14 g sodium acetate in 2,450 ml water and 288 ml hexane then cooled to 10°C, aged 20 min, filtered and washed with 800 ml water containing 1 g sodium acetate, followed by 220 ml hexane.

The wet cake (ca. 200 g) is charged to a cold (10°C) mixture of 13.7 g sodium acetate in 184 ml water and 440 ml acetone and cooled to 0°–5°C. A solution of 27 g Halane in 120 ml acetone is added keeping the temperature below 5°C. The mixture is aged 45 min at 0°–5°C, then a solution of 9.2 g sodium bisulfite in 132 ml water is added and the mixture is drawned into 2200 ml water, slowly over a period of 30 min and cooled to 0°–5°C, aged 1 hr, filtered and dried at 45°–50°C in vacuum oven. Yield: 107.2 g (97.1 w/w; 89.5% Th).

Reaction with triethyl orthoacetate to form a 3-enol ether and subsequent $\Delta^{4,6}$ formation.

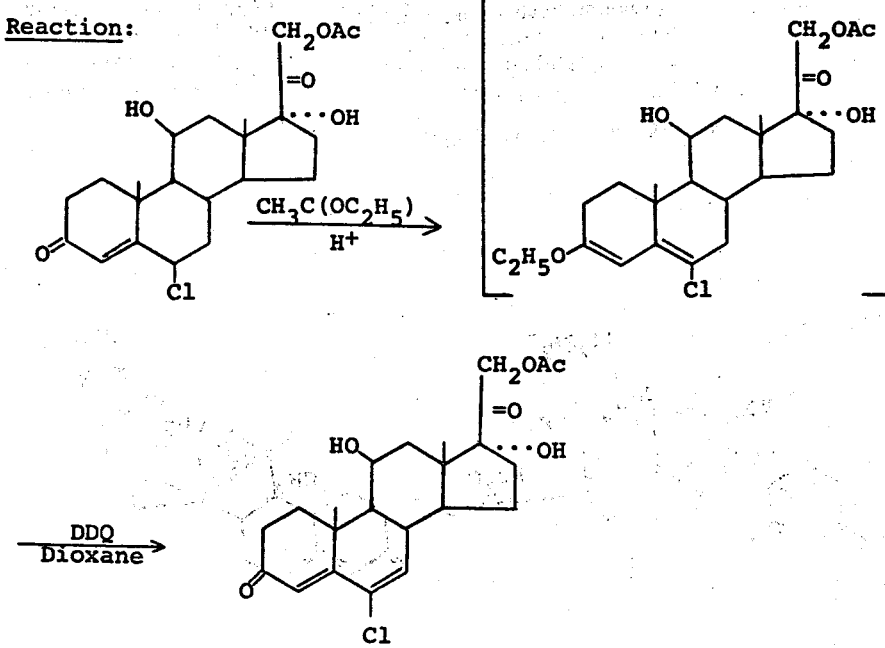

Procedure:

A 2-liter flask is charged with 104 g (0.237 mole) 6β-chloro-11β,17α,21-trihydroxypregn-4-ene-3,20-dione-21-acetate (from the previous step), 500 ml 1,2-dimethoxyethane and 3.03 g p-toluenesulfonic acid and aged for 30 min at 20°–25°C. 500 ml ethanol is added followed by 91.4 g (0.563 mole) triethylorthoacetate. The reaction mixture becomes dark red and is aged at 20°–25°C for 40 min then cooled to 15°C and a solution of 13 g sodium acetate in 640 ml water is added. The temperature is kept below 20°C and 220 ml methylene chloride are added followed by 1000 ml water added slowly, keeping the temperature below 25°C. The mixture is agitated for 15 min and lower organic layer is separated. The upper aqueous layer is extracted with 3, 75 ml portions of methylene chloride. The organic fractions are combined and washed with a solution of 1.3 g sodium acetate in 260 ml water. The methylene chloride extract (ca. 900 ml total) is separated and concentrated under vacuum to approx. 400 ml and, while distilling, a mixture of 850 ml dioxane and 1.3 ml pyridine is added keeping the volume approx. 400–450 ml. The mixture is distilled to final volume of 400 ml (no methylene chloride should be present at this point) and 300 ml dioxane are added. The mixture is cooled to 10°C and 65 ml water are added, then cooled to 0°–5°C. A solution of 75 g DDQ in 300 ml dioxane is added over a period of 1 hr keeping the temperature at 0°–5°C. The addition funnel is washed with 30 ml dioxane and the mixture is aged at 0°–5°C for 30 min. A solution of 30.4 g sodium bisulfite in 87 ml water is added, keeping the temperature below 10°C. The slurry is concentrated under vacuum to 600 ml. The slurry is charged slowly, under vigorous agitation, to 3000 ml water than cooled to 10°C and aged 3 hr. The product mixture is filtered and washed with water. The wet solid is charged to 1500 ml methylene chloride, agitated for 1 hr, filtered and washed with 100 ml methylene chloride. The solid is charged to 400 ml methylene chloride, agitated 20 min, filtered and washed with 100 ml methylene chloride. The methylene chloride solutions are combined and agitated with 1000 ml water. The organic layer is separated and the water layer is extracted with 50 ml methylene chloride. The methylene chloride extracts are concentrated to 400 ml and while distilling 1000 ml acetone are added keeping the volume approx. 360–400 ml. The slurry is distilled to final volume of 300 ml and cooled to 0°– 5°C, aged 30 min, filtered and washed with 82 ml cold (0°–5°C) acetone. The product is dried in vacuum at 50°C. Yield: 80.3 g (77.2 w/w; 77.5% Th)

Δ¹ Formation and subsequent hydrolysis

Reactions:

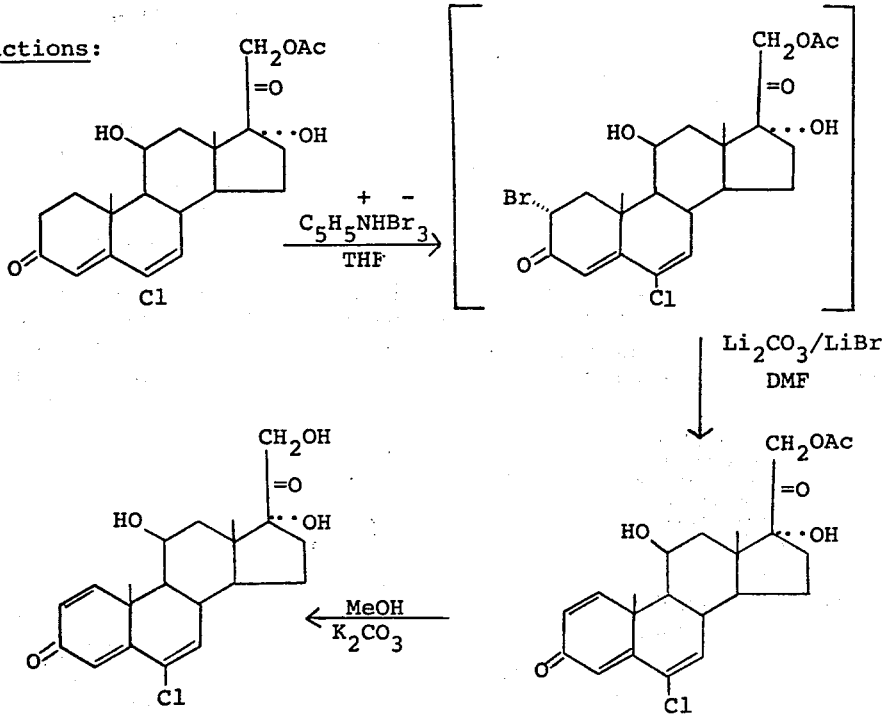

Procedure:

Fifty grams of RS-4232 acetate (from the previous step contains ca. 10% acetone) are charged to 350 ml methylene chloride. Thirty grams of neutral alumina are added and the mixture agitated for 1 hr. The alumina is filtered and the solution is concentrated to a volume of 50 ml. Tetrahydrofuran (400 ml) is added and the distillation is continued until a boiling point of ca. 65°C is reached. The mixture is cooled to 25°C and a solution of 34 g of pyridinium hydrobromide perbromide in 130 ml of tetrahydrofuran is added. The reaction is stirred at 25°C for 20 minutes and 3 ml of acetone is added. The reaction mixture is filtered and the filtrate is concentrated to a volume of 50 ml. Dimethylformamide (400 ml) is added followed by 22.5 g of lithium carbonate and 8.1 g of lithium bromide. The system is purged with nitrogen and the reaction mixture is heated to 105°C for 2½ hours, concentrated under vacuum to 200 ml. cooled to 60°C and 50 ml of acetic acid are added, followed by 70 ml of water. The reaction mixture is drowned slowly into 1600 ml of water. After 1 hour at 25°C the product was filtered and washed with water. The product was dried in vacuum at 60°C. Yield: 41.5 g (83 w/w). The product is crystallized twice from acetone. Purification yield: 78.8 w/w.

6-chloro-11β,17α,21-trihydroxy pregna-1,4,6-trien-3,20-dione is formed by transesterification in anhydrous methanol in the presence of a small amount of potassium carbonate.

EXAMPLE IX

The product of Example 8 is followed to obtain 6-chloro-11β,17α,21-trihydroxypregna-4,6-diene-3,20-dione-21-acetate which is transesterified to the corresponding 21-hydroxy compound by reacting with anhydrous methanol in the presence of a small amount of potassium carbonate.

EXAMPLE X

This Example shows a method for $\Delta^1$ formation using microbiological means (i.e. growing cells with a hydrogen acceptor)

A. Fermentation

A culture of Arthobacter simplex NRRLB-8055 is grown for 6 days at 28°C on an agar slant of the following composition (A):

| Nutrient agar (Difco) | 20 gm. |
| Glucose | 10 gm. |
| Yeast extract (Difco) | 10 gm. |
| Distilled water | 1 liter |

A loop full of the surface growth of the slant is used to inoculate each of two 300 ml. nephlo-culture flasks (Bellco Inc.), each containing 50 ml. of the following sterile nutrient medium (B):

| Corn steep liquor | 5 | gm. |
| Yeast extract (Difco) | 1 | gm. |
| Cerelose (pract. glucose monohydrate) | 0.5 | gm. |
| Distilled water pH 7 | 1 | liter |

The flasks are incubated at 28°C on a rotary shaker at 280 r.p.m. using a 1 inch stroke. Incubation is complete in 24 hours or when culture turbidity reaches 165–180 Klett Units as measured on a Klett-Summerson photoelectric colormeter equipped with a No. 66 filter and zero adjusted with sterile medium. Thereafter, the entire contents of both flasks are used to inoculate 900 ml. of freshly sterilized medium B contained in a 2-liter glass fermentor jar. Incubation of the fermentor jar is continued at 28°C while aeration is maintained at ½ volume air/volume medium/minute and agitation is held at 300 r.p.m. After 24 hours, 500 mg. of 6-chloro-11β,17α,21-trihydroxy-pregna-4,6-dione 3,20-dione (prepared as shown in Examples 8 and 9) is added to the fermentation as an ethanolic solution (25 mg./0.4 ml. ethanol). At the same time, 26.4 mg. of menadione sodium bisulfite is also added to the fermentation as a filtered, sterilized aqueous solution (26.4 mg./10 ml.). Incubation is continued as before. The reaction is complete in 3 to 5 hours.

B. Isolation and Characterization

The fermentation broth is extracted three times with 500 ml. portions of chloroform. The combined chloroform extracts are dried over anhydrous sodium sulfate and concentrated to dryness under vacuum. The resultant semi-crystalline residue is purified by chromatography over silica gel. The product is eluted with mixtures of chloroform and acetone. The fractions containing the desired product are pooled and evaporated to dryness to give 475 mg. (yield 95% of theory) of 6-chloro-$\Delta^{1,4,6}$-pregnatrien-11β,17α,21-triol-3,20-dione which is then crystallized from isopropyl acetate.

In like manner, substituting menadione and tetramethyl-p-benzoquinone for menadione sodium bisulfite produces a similar conversion of 6-chloro-$\Delta^{4,6}$-pregnadiene-11β,17α,21-triol-3,20-dione to 6-chloro-$\Delta^{1,4,6}$-pregnatriene-11β,17α,21-triol-3,20-dione.

EXAMPLE XI

An inoculum of Arthobacter simplex is prepared as in Example 10.

Five ml. of the 24 hour seed culture is then used to inoculate for 250 ml. Erlenmeyer flasks, each containing 50 ml. of Medium B (Example 1). The flasks are incubated at 28°C on a rotary shaker at 280 r.p.m. using a 1 inch stroke. After 24 hours, 25 mg. of 6-chloro-$\Delta^{4,6}$-pregnadiene-11β,17α,21-triol-3,20-dione (prepared in Examples 8 and 9) dissolved in 0.4 ml. of ethanol is added to each flask. At the same time one flask receives 0.78 mg. of 2-isopropyl-5-methyl-p-benzoquinone in 0.2 ml. ethanol. A second flask receives 0.83 mg. of 2-hydroxy-1,4-naphthoquinone and a third flask receives 1.2 mg. of the sodium salt of 2,6-dichloroindophenol dissolved in 0.5 ml. H$_2$O. A hydrogen acceptor is not added to the fourth flask which serves as a control. Thin layer chromatographic analyses of solvent extracted samples taken after 7 and 24 hours contact time indicate an increased rate and percent formation of the product 6-chloro-$\Delta^{1,4,6}$-pregnatriene-11β,17α,21-triol-3,20-dione when compared to the untreated control.

EXAMPLE XII

In this process, the procedure of Example I is followed except that 2 grams of trifluoroacetic acid is used instead of PTSA as the acid catalyst. Similar yields are obtained.

EXAMPLE XIII

In this process the procedure of Example I is followed except that 2 grams of sulfuric acid is used instead of PTSA as the acid catalyst. Similar yields are obtained.

I claim as my invention:

1. A process which comprises reacting a compound chosen from the group represented by the formula

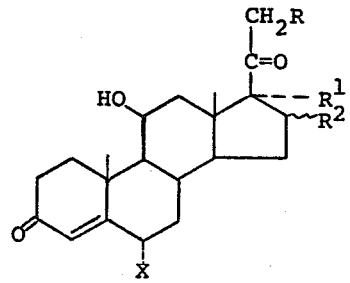

wherein
R is —H, —OH, lower alkyl ether of 1–6 carbons, or lower alkyl ester of 1–6 carbons;
R$^1$ is —H, —OH or lower alkyl ester of 1 to 6 carbons;
R$^2$ is —H, α—CH$_3$, or β—CH$_3$;
X is H, F, Cl, or Br and
R$^1$ and R$^2$ together may be

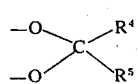

with triethyl orthoacetate in the presence of a catalytic amount of a strong acid in a solvent which consists essentially of about 40% by weight or more ethanol and about 60% by weight or less of a compatible, oxygenated hydrocarbon liquid.

2. The process of claim 1 wherein R is a lower alkyl ester, $R^1$ is OH and X and $R^2$ are H.

3. The process of claim 2 wherein said solvent system consists at least about 50% by weight or more of ethanol and about 50% by weight or less glyme, R is acetate, and said acid catalyst is p-toluene sulfonic acid or trifluoroacetic acid.

4. The process of claim 1 wherein X is chloro and said 6α-chloro compound is formed from the corresponding 6α-chloro compound by placing said corresponding 6β-chloro compound in contact with said strong acid in said solvent for a time period sufficient to convert substantially all of said 6β-chloro to 6α-chloro, then reacting said 6α-chloro compound with said triethyl orthoacetate.

5. A process which comprises reacting cortisol-21-acetate with triethyl orthoacetate in the presence of a catalytic amount of p-toluene sulfonic acid or trifluoroacetic acid in a solvent which consists essentially of about 50% by weight of ethanol and about 50% by weight of glyme at about 20°C to about 40°C to form the corresponding 3-enol ethyl ether, said 3-enol ether being substantially free of a $\Delta^{9(11)}$ dehydrogenation product.

6. A process which comprises reacting cortisol with triethyl orthoacetate in the presence of a catalytic amount of p-toluene sulfonic acid or trifluoroacetic acid in a solvent which consists essentially of about 50% by weight of ethanol and about 50% by weight of glyme at about 20°C to about 40°C to form the corresponding 3-enol ethyl ether, said 3-enol ether being substantially free of a $\Delta^{11(9)}$ dehydrogenation product.

7. A process which comprises
   a. reacting a first compound chosen from the group represented by the formula

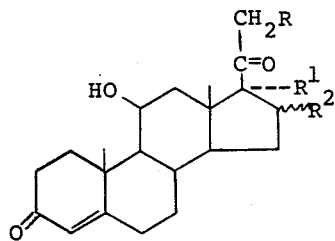

wherein
   R is H, OH, lower alkyl ether of 1–6 carbons or lower alkyl ester of 1–6 carbons;
   $R^1$ is H, OH or lower alkyl ester of 1–6 carbons;
   $R^2$ is H, αCH$_3$ or βCH$_3$
   $R^1$ and $R^2$ together are

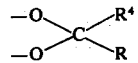

wherein $R^4$ and $R^5$ are each a hydrocarbon of 1 to 4 carbons with triethylorthoacetate in the presence of a catalytic amount of a strong acid in a solvent which consists essentially of about 40% by weight or more ethanol and about 60% by weight or less of a compatible, oxygenated hydrocarbon liquid to form a reaction product which is a 3-enol-ether, and
   b. subsequently reacting said reaction product with a brominating or chlorinating agent to form a 3-oxo-6β-halo-$\Delta^4$-steroid product.

8. The process of claim 7 wherein said first compound is a cortisol-21-alkyl ester, said solvent is a mixture of about 50 by weight ethanol and 50% by weight glyme, said catalyst is trifluoroacetic acid or p-toluenesulfonic acid, and said reaction product from (a) is reacted with a chlorinating agent which is N-chlorosuccinimide or dimethyl-N,N'-dichlorohydantoin.

9. A process which comprises
   a. reacting cortisol-21-acetate with triethyl orthoacetate in the presence of a catalytic amount of a strong acid catalyst in a solvent which consists essentially of about 40%w or more ethanol and about 60%w or less of a compatible, aliphatic ether or cyclic ether which is freely miscible with ethanol in all proportions to form a reaction product which is a 3-enol ether;
   b. subsequently reacting said 3-enol ether from (a) with a brominating or chlorinating agent to form a 6β-bromo or chloro-cortisol-21-acetate;
   c. reacting said 6β-bromo or chloro-cortisol-21-acetate of step (b) with a catalytic amount of a strong acid catalyst in glyme to form 6α-bromo or chloro-cortisol-21-acetate;
   d. subsequently reacting said 6α-bromo or chloro-cortisol-21-acetate with triethyl orthoacetate in a solvent which is a mixture of about 40%w or more ethanol and 60%w or less of a compatible, aliphatic ether or cyclic ether which is freely miscible with ethanol in all proportions in the presence of a catalytic amount of a strong acid catalyst to form a reaction product which is the corresponding 3-enol ether;
   e. forming 6-bromo or chloro-11β,17α,21-trihydroxy pregna-4,6-diene-3,20-dione-21-acetate; and
   f. forming 6-bromo or chloro-11β,17α,21-trihydroxy pregna-1,4,6-triene-3,20-dione-21-acetate.

10. The process of claim 9 wherein
    said strong acid catalyst in steps (a), (c) and (d) is trifluoroacetic acid or p-toluenesulfonic acid;
    said brominating or chlorinating agent in step (b) is a chlorinating agent;
    said compatible aliphatic or cyclic ethers in steps (a) and (d) are glyme, and
    the product of step (e) is formed by reacting said 3-enol ether of step (d) with 2,3-dichloro-4,5-dicyanobenzoquinone in dioxane.

11. The process of claim 10 wherein
    said chlorinating agent is N-chlorosuccinimide or dimethyl-N,N'-dichlorohydantoin.

12. The process of claim 9 wherein
    said step (f) is carried out by first reacting said compound from step (e) with a brominating agent to form a 2-bromo compound then reacting said 2-bromo compound with a dehydrobrominating agent.

13. The process of claim 12 wherein
    step (f) comprises reacting the product from step (e) with pyridinium hydrobromide perbromide and tetrahydrofuran to form a 2-brominated product then reacting said 2-brominated product with lithium carbonate and lithium bromide in dimethylformamide.

14. The process of claim 9 which comprises subsequently converting the product of step (f) to 6-bromo or chloro-11β,17α,21-trihydroxypregn-1,4,6-triene-3,20-dione.

15. The process of claim 14 wherein said conversion is done by transesterification of the product of step (f) with methanol and potassium carbonate.

16. A process which comprises
 a. reacting cortisol-21-acetate with triethyl orthoacetate in the presence of a catalytic amount of a strong acid catalyst in a solvent which consists essentially of about 40%w or more ethanol and about 60%w or less of a compatible aliphatic ether or cyclic ether which is freely miscible with ethanol in all proportions to form a reaction product which is a 3-enol ether;
 b. subsequently reacting said 3-enol ether from (a) with a brominating or chlorinating agent to form a 6β-bromo or chloro-cortisol-21-acetate;
 c. reacting said 6β-bromo or chloro-crotisol-21-acetate of step (b) with a catalytic amount of a strong acid catalyst in glyme to form 6α-bromo or chloro-cortisol-21-acetate;
 d. subsequently reacting said 6α-bromo or chloro-cortisol-21-acetate with triethyl orthoacetate in a solvent which is a mixture of about 40%w or more ethanol and 60%w or less of a compatible, aliphatic ether or cyclic ether which is freely miscible with ethanol in all proportions in the presence of a catalytic amount of a strong acid catalyst to form a reaction product which is the corresponding 3-enol ether;
 e. forming 6-bromo or chloro-11β,17α,21-trihydroxy-4,6-diene-3,20-dione-21-acetate;
 f. subsequently converting said 21-acetate product from (e) to 6-bromo or chloro-11β,17α,21-trihydroxypregn-4,6-diene-3,20-dione; and
 g. microbiologically converting the products from (f) to 6-bromo or chloro-11β,17α,21-trihydroxypregn-1,4,6-triene-3,20-dione.

17. The process of claim 16 wherein
said strong acid catalyst in steps (a), (c) and (d) is trifluoroacetic acid or p-toluenesulfonic acid;
said brominating or chlorinating agent in step (b) is a chlorinating agent;
said compatible aliphatic ether or cyclic ethers in steps (a) and (d) are glyme; and
the product of step (e) is formed by reacting said 3-enol ether of step (d) with 2,3-dichloro-4,5-dicyanobenzoquinone in dioxane.

18. The process of claim 17 wherein said chlorinating agent is n-chlorosuccinimide or dimethyl-N,N'-dichlorohydantion.

* * * * *

UNITED STATES PATENT OFFICE
CERTIFICATE OF CORRECTION

Patent No. 3,956,349           Dated May 11, 1976

Inventor(s) PASQUALE G. GALLEGRA

It is certified that error appears in the above-identified patent and that said Letters Patent are hereby corrected as shown below:

Column 24, line 11, change "for" to --four--.

Column 24, after line 68, insert --wherein $R^4$ and $R^5$ are hydrocarbons of 1 to 4 carbons--.

Signed and Sealed this

First Day of February 1977

[SEAL]

Attest:

RUTH C. MASON
*Attesting Officer*

C. MARSHALL DANN
*Commissioner of Patents and Trademarks*